US006585710B1

(12) United States Patent
Brisebois (10) Patent No.: US 6,585,710 B1
(45) Date of Patent: Jul. 1, 2003

(54) SANITARY NAPKIN WITH STIFF SIDE FLAPS

(75) Inventor: Henri Brisebois, Lachenaie (CA)

(73) Assignee: Johnson & Johnson, Inc. (CA)

( * ) Notice: Subject to any disclaimer, the term of this patent is extended or adjusted under 35 U.S.C. 154(b) by 0 days.

(21) Appl. No.: 09/714,651

(22) Filed: Nov. 16, 2000

(51) Int. Cl.$^7$ ............................................... A61F 13/15
(52) U.S. Cl. ............................ 604/385.04; 604/385.03; 604/385.01
(58) Field of Search ........................ 604/385.04, 385.01, 604/385.03, 385.05, 385.28

(56) References Cited

U.S. PATENT DOCUMENTS

| | | | | |
|---|---|---|---|---|
| 4,285,343 A | * | 8/1981 | McNair | 128/287 |
| 4,608,047 A | * | 8/1986 | Mattingly | 604/387 |
| 4,701,177 A | * | 10/1987 | Ellis et al. | 604/385 |
| 5,125,918 A | | 6/1992 | Seidy | 604/386 |
| 5,308,346 A | * | 5/1994 | Sneller et al. | 604/385.2 |
| 5,387,210 A | * | 2/1995 | Murakami | 604/396 |
| 5,447,507 A | * | 9/1995 | Yamamoto | 604/385.2 |
| 5,454,804 A | | 10/1995 | Widlund | 604/389 |
| 5,490,847 A | * | 2/1996 | Correa et al. | 604/387 |
| 5,591,147 A | | 1/1997 | Couture-Dorschner et al. | 604/369 |
| 5,650,223 A | * | 7/1997 | Weinberger et al. | 442/62 |
| 6,315,766 B1 | * | 11/2001 | Drevik | 604/387 |

FOREIGN PATENT DOCUMENTS

| | | | |
|---|---|---|---|
| EP | 0314535 A | 5/1989 | |
| EP | 0940133 A | 9/1999 | |
| EP | 0968696 A | 1/2000 | |
| FR | 2756728 A | 6/1998 | |
| WO | WO 92/07536 | 5/1992 | A61F/13/56 |
| WO | WO 97/36563 | 10/1997 | A61F/13/15 |
| WO | WO 99/58092 | 11/1999 | A61F/13/15 |

* cited by examiner

*Primary Examiner*—Weilun Lo
*Assistant Examiner*—Jacqueline F. Stephens (57) ABSTRACT

A sanitary napkin having a main body including at least three superposed functional layers, namely a fluid permeable body facing layer, an absorbent layer and a liquid impermeable undergarment facing layer. The sanitary napkin has flaps adapted to be folded around the edges of an undergarment of a wearer. The flaps are physically associated with respective longitudinal sides of the main body and are characterized by a rigidity sufficient to cause the longitudinal sides to fold upwardly when the flaps are parted to receive between them the crotch portion of the undergarment of the user. The upwardly folded longitudinal sides form upstanding barriers to limit the likelihood of failure as a result of side leakage.

12 Claims, 6 Drawing Sheets

SANITARY NAPKIN WITH STIFF SIDE FLAPS

FIELD OF THE INVENTION

This invention relates to disposable absorbent products for absorbing body fluids and, in particular, to sanitary napkins adapted to be worn against the perineal region of the body and held in place in the crotch portion of the undergarment when worn by the user. In a specific non-limiting example of the inventive principle, the sanitary napkin is provided with a pair of stiff flaps that are associated to the longitudinal sides of the sanitary napkin and cause the sides to bend upwardly as they are parted during placement of the sanitary napkin on the undergarment of the wearer. The upwardly bent sides form upstanding barriers that impede body exudate discharged on the sanitary napkin from leaking past the sides of the sanitary napkin.

BACKGROUND OF THE INVENTION

Sanitary napkins are prone to fail when body exudate is discharged on the napkin at a higher rate than that which the napkin can take up. When such failure occurs, body exudate usually leaks at the sides of the sanitary napkin and soils the undergarment.

One approach to solve this problem has been described in the international patent application PCT/SE91/00735 filed on Oct. 31, 1991 and published on May 14, 1992 which teaches a sanitary napkin with side flaps that in use are folded over the edges of the crotch portion of the undergarment. A portion of each side flap is bonded in a face-to-face relationship with the flange seal of the sanitary napkin that surrounds the absorbent system. When the napkin is worn, the side flaps are pulled out from the sides of the central absorbent pad causing flange seal to raise into an upstanding barrier. However, in practice, the upstanding barrier may not always be created. For example, if the width of the central absorbent pad is not substantially less than the width of the user's undergarment, it will not be possible for the flaps to be pulled and maintained in an outward orientation with respect to the absorbent pad. If the flaps are not maintained in this position, the upstanding barrier will not be formed.

Against this background, there exists a need in the industry to provide a sanitary napkin that offers a reduced likelihood of side failure.

SUMMARY OF THE INVENTION

In accordance with the present invention, there has been provided a sanitary napkin having a main body including at least three superposed functional layers, namely a fluid permeable body facing layer, an absorbent layer and a liquid impermeable undergarment facing layer. The main body has a pair of opposite longitudinal sides and a pair of opposite transverse sides. The sanitary napkin has at least one flap that is affixed to or otherwise physically associated with each longitudinal side of the main body. The flap is characterized as having a rigidity that is sufficient to cause the longitudinal side to fold upwardly when the flap is subjected to an effort causing outward displacement of the flap from a first position toward a second position, in the first position the flap acquiring a more acute angular relationship to the liquid impermeable undergarment facing layer than in the second position.

One benefit of this sanitary napkin is the formation of an upstanding barrier on the main body that impedes the lateral flow of body exudate and can, therefore, reduce the likelihood of failures. The upstanding barrier results from the outward displacement of the flap that is normally effected when the sanitary napkin is installed on the undergarment of the wearer. The longitudinal side of the main body is maintained in the upwardly oriented position during the use of the sanitary napkin since the flap is restrained from moving back toward the liquid impermeable undergarment facing layer by the undergarment.

Optionally, the main body is manufactured such that the longitudinal side has a resiliency sufficient to urge the flap into mechanical engagement with the crotch portion of the undergarment when the effort causing outward displacement of the flap from the first position toward the second position ceases.

Another option is to provide the sanitary napkin with a pair of stiff flaps, each flap being associated with a respective longitudinal side. The upstanding barriers on the main body are formed when the flaps are parted to install the sanitary napkin on the crotch portion of the undergarment and they are maintained in this position during the use of the sanitary napkin.

In a specific non-limiting example of implementation, the main body is generally rectangular with substantially rounded ends. When the main body is of such a conformation, the transverse sides are the shorter opposing sides and will generally have an arcuate shape. The longitudinal sides are the longer opposing sides and will generally be arcuate, typically inwardly arcuate. It should be understood, however, that the shape of such sides is not essential to the invention, and thus the transverse or the longitudinal sides could either be arcuate or straight.

The main body is of a laminate construction and has at least three functional layers, namely: the fluid permeable body facing layer, the absorbent layer and a liquid impermeable undergarment facing layer. The fluid permeable body-facing layer is usually designated as "cover layer". The cover layer is fluid-permeable, and thus will permit the body exudate discharged on the main body to pass through it and into the layers below.

The absorbent layer underlies the cover layer and is often referred to as an "absorbent system". The absorbent layer may comprise a single layer or a composite layer combining multiple layers or additional structures; the primary purpose of all of which being to absorb and retain body exudate. Many different absorbent systems are known in the art.

Underneath the absorbent system is the liquid impermeable undergarment-facing layer, also called "barrier layer". The primary purpose of the barrier layer is to prevent exudate absorbed within the sanitary napkin from egressing the sanitary napkin on the opposite side from which it was absorbed. The barrier layer is thus impervious to liquid but could be made pervious to gases to provide breathability.

The cover layer and the barrier layer are joined to one another around the periphery of the sanitary napkin to form a flange seal enclosing the absorbent system, and thus forming a structurally integral sanitary napkin. Other conventional methods of adhering or uniting the various components of the article together, such as adhesive between the components, are all also within the scope of the present invention.

The sanitary napkin has a pair of flaps each flap affixed to a respective opposite longitudinal side of the main body. Each flap has a proximal end portion and a distal end portion. The proximal end portion is the portion of the flap that is physically attached to the main body while the distal end portion is the opposite end portion of the flap that is remote from the main body. Each flap is attached to a portion of the flange seal that forms a respective longitudinal side of the main body. More specifically, the surface of the flap that faces the barrier layer is attached in a face to face relationship to the lower surface of the flange seal (the surface of the flange seal that is oriented toward the undergarment of the wearer).

At least a portion of each flap is constructed of a material that is sufficiently rigid such that when the flaps are parted to allow the sanitary napkin to be installed on the crotch portion of the undergarment, they will raise the flange seal to form a pair of opposite upstanding barriers. The stiffness or rigidity of the flaps should be sufficient to cause the flange seal to fold upwardly when the flaps are parted. In general, the more rigid the flange seal, the stiffer the flaps should be. In a specific example, the flaps are formed from a foam material. Alternatively, the flaps can be formed of a material that is not inherently rigid but to which rigidity has been imparted by specific treatments or by addition of specific structures. One specific treatment to impart or enhance rigidity is embossing. Embossing has the effect of densifying the material and thus renders it less pliable. Alternatively, specific structures such as additional layers of material can be added to reinforce the tab.

BRIEF DESCRIPTION OF THE DRAWINGS

A detailed description of examples of implementation of the present invention is provided hereinbelow with reference to the following drawings, in which.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

Figure 1:
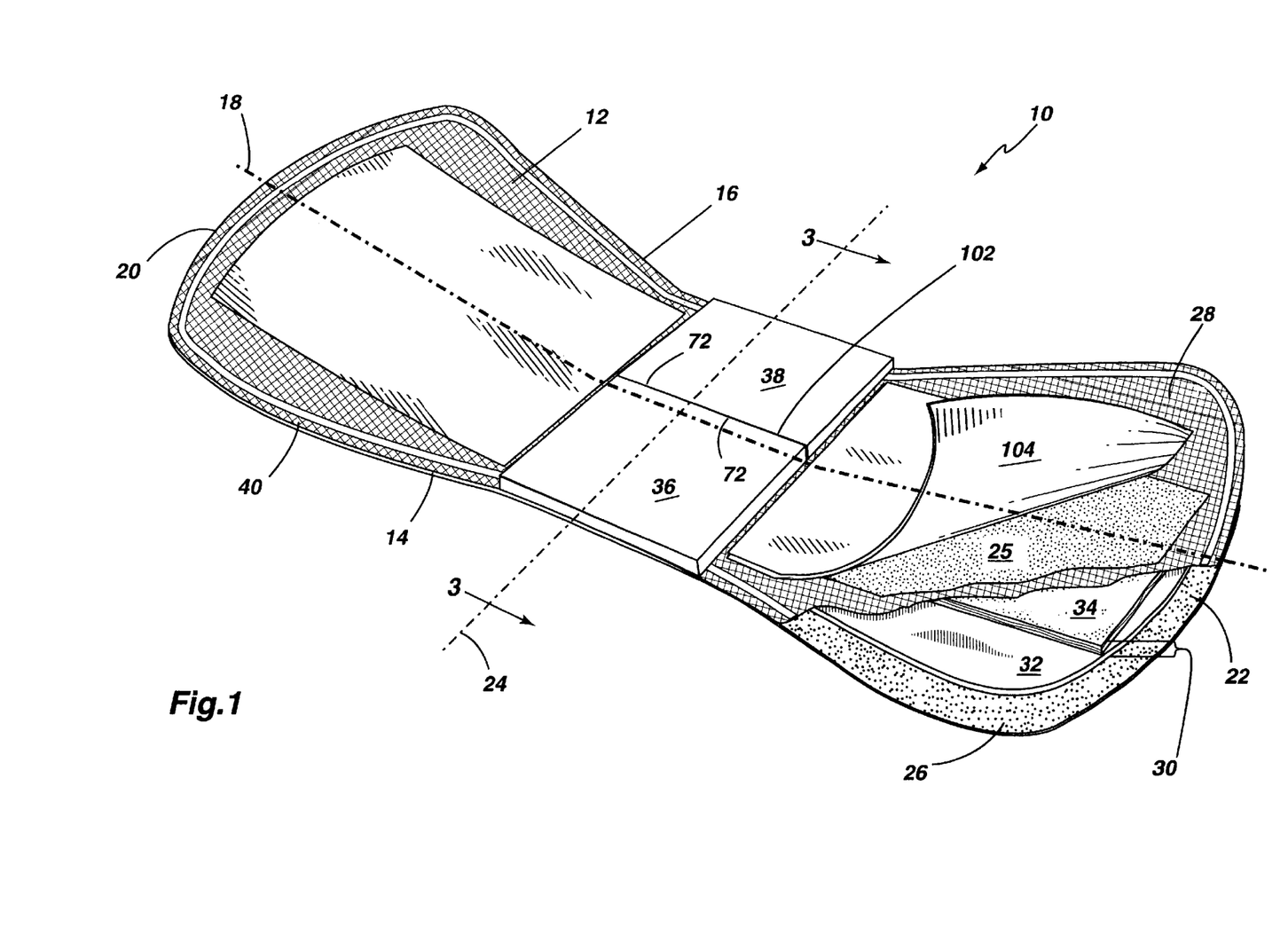
FIG. 1 is a bottom perspective view of a sanitary napkin constructed in accordance with a specific example of implementation of the present invention.

With reference to FIG. 1, there is shown an example of implementation of a sanitary absorbent article of the present invention, namely a disposable sanitary napkin 10. The sanitary napkin 10 comprises a main body 12. The main body 12 has two generally opposing longitudinal sides 14, 16 and an imaginary longitudinal centerline 18 running down the center of the napkin 10, generally equidistant from the longitudinal sides 14, 16 and thus bisecting the main body 12 in two identical halves. The longitudinal sides 14, 16 are concavely arcuate.

The main body 12 also has two generally opposing transverse sides, 20, 22 which are convexly arcuate. An imaginary transverse centerline 24 runs across the napkin 10, perpendicular to the longitudinal centerline 18, and thus bisects the main body 12 in two identical halves.

Figure 3:
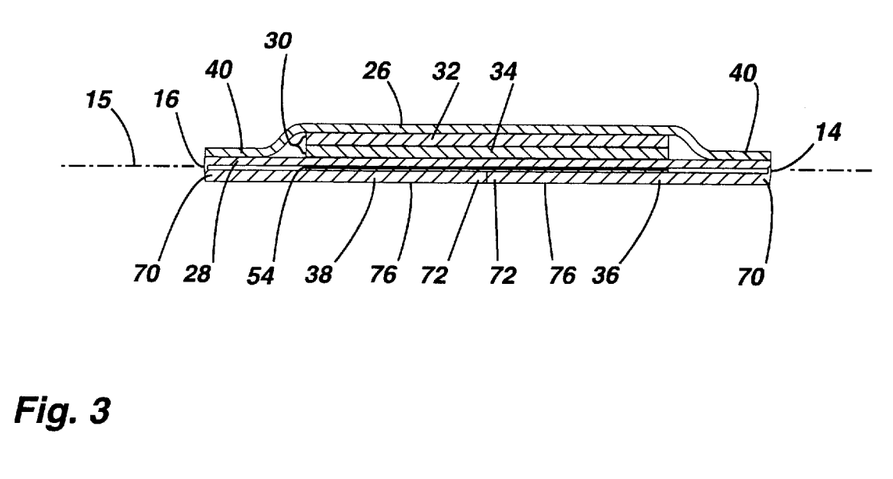
FIG. 3 is a cross-sectional view taken along lines 3–3 in FIG. 1, the cross-sectional illustration being inverted with relation to the orientation of the sanitary napkin in FIG. 1.

With reference to FIGS. 1 and 3, the sanitary napkin 10 is a laminate structure and the main body 12 has a cover layer 26 which will face the body of a wearer when the napkin 10 is in use; a barrier layer 28, which will face the environment (i.e. away from the body of the wearer, and in almost all cases the wearer's undergarment) when the sanitary napkin 10 is in use; and a layer-like absorbent system 30 therebetween. The absorbent system 30 comprises a first absorbent layer, commonly called "transfer layer" 32 positioned immediately underneath the cover layer 26 and a second absorbent layer, commonly called "absorbent core" 34 that is located between the first absorbent layer 32 and the barrier layer 28.

The cover layer 26 and the barrier layer 28 are joined along their marginal portions to form an enclosure or flange seal 40 that maintains the absorbent system 30 captive. The joint may be made by means of adhesives, heat-bonding, ultrasonic bonding, radio frequency sealing, mechanical crimping, and the like and combinations thereof.

In the example of implementation depicted in the drawings, the flange seal 40 is continuous around the absorbent system 30. Optionally, the flange seal 40 may be discontinuous, in other words the cover layer 26 and the barrier layer 28 remain unattached to one another at some peripheral areas of the sanitary napkin.

The main body 12 is provided with a pair of flaps 36, 38 that are affixed to the respective longitudinal sides 14, 16. The flaps may be either directly affixed to the sides of the main body or may be affixed through one or more intermediate components.

Each of the constituent elements of the sanitary napkin 10 will be described in further detail hereinbelow.

Cover Layer

The cover layer 26 may be a relatively low density, bulky, high-loft non-woven web material. The cover layer 26 may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. An example is the non-woven cover layer of sanitary napkins sold by Johnson & Johnson Inc. of Montreal, Canada under the trademark Stayfree Ultra-Thin Cottony Dry Cover.

Bi-component fibers may be made up of a polyester core and a polyethylene sheath. The use of appropriate bi-component materials results in a fusible non-woven fabric. Examples of such fusible fabrics are described in U.S. Pat. No. 4,555,432 issued Nov. 28, 1985 to Mays. Using a fusible fabric increases the ease with which the cover layer may be mounted to the underlying first absorbent layer and/or to the barrier layer.

Although the individual fibers comprising the cover layer 26 may not be particularly hydrophilic, the cover layer 26 preferably has a relatively high degree of wettability. The cover material should also contain a great number of relatively large pores. This is so because the cover layer 26 is intended to take-up body fluid rapidly and transport it away from the body and the point of deposition. Advantageously, the fibers which make up the cover layer 26 should not lose their physical properties when they are wetted, in other words they should not collapse or lose their resiliency when subjected to water or body fluid. The cover layer 26 may be treated to allow fluid to readily pass through it. The cover layer 26 also functions to transfer the fluid quickly to the other layers of the absorbent system 30. Thus, the cover layer 26 is advantageously wettable, hydrophilic, and porous. When composed of synthetic hydrophobic fibers such as polypropylene or bi-component fibers, the cover layer 26 may be treated with a surfactant to impart the desired degree of wettability.

Alternatively, the cover layer 26 can also be made of polymeric film having large pores. Because of such high porosity, the film accomplishes the function of quickly transferring body fluid to the inner layers of the absorbent system. Apertured co-extruded films such as those described in U.S. Pat. No. 4,690,679 and available on sanitary napkins sold by Johnson & Johnson Inc. of Montreal, Canada could be useful as cover layers in the present invention.

The cover layer 26 may be embossed to the absorbent system 30 in order to aid in promoting fluid transport by fusing the cover layer to the next layer. Such fusion may be effected locally, at a plurality of sites, or over the entire contact surface of cover layer 26 with absorbent system 30. Alternatively, the cover layer 26 may be attached to the absorbent system 30 by other means such as with adhesive.

Absorbent System—First Absorbent Layer (Transfer Layer)

Adjacent to the cover layer 26 on its inner side and bonded to the cover layer 26 is the first absorbent layer 32 that forms part of the absorbent system 30. The first absorbent layer 32 provides the means of receiving body fluid from the cover layer 26 and holding it until an underlying second absorbent layer has an opportunity to absorb the fluid.

The first absorbent layer 32 is, preferably, more dense than and has a larger proportion of smaller pores than the cover layer 26. These attributes allow the first absorbent layer 32 to contain body fluid and hold it away from the outer side of the cover layer 26, thereby preventing the fluid from re-wetting the cover layer 26 and its surface. However, the first absorbent layer 32 is, preferably, not so dense as to prevent the passage of the fluid through it and into the underlying second absorbent layer 34. These types of absorbent layers are commonly known as fluid transfer layers or acquisition layers.

The first absorbent layer 32 may be composed of fibrous materials, such as wood pulp, polyester, rayon, flexible foam, or the like, or combinations thereof. The first absorbent layer 32 may also comprise thermoplastic fibers for the purpose of stabilizing the layer and maintaining its structural integrity. The first absorbent layer 32 may be treated with surfactant on one or both sides in order to increase its wettability, although generally the first absorbent layer 32 is relatively hydrophilic and may not require treatment. The first absorbent layer 32 is preferably bonded on both sides to the adjacent layers, i.e. the cover layer 26 and an underlying second absorbent layer 34. An example of a suitable first absorbent layer is a through air bonded pulp sold by BUCKEYE of Memphis, Tenn. under the designation VIZORB 3008.

Absorbent System—Second Absorbent Layer (Absorbent Core)

Immediately adjacent to and bonded to the first absorbent layer 32 is the second absorbent layer 34.

In one non-limiting example of implementation, the second absorbent layer 34 is a blend or mixture of cellulosic fibers and superabsorbent disposed in and amongst fibers of that pulp. The second absorbent layer 34 can contain any superabsorbent polymer (SAP); SAPs being well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Superabsorbent polymer particles that could be used for the present invention are crosslinked polyacrylates, such as the product offered by Sumitomo Seika Chemicals Co., Ltd. Of Osaka, Japan, under the designation of SA60N Type II*, and the product offered by Chemdal International, Inc. of Palatine, Ill., under the designation of 2100A*.

In one specific and non-limiting example of implementation, the cellulosic fiber for use in the second absorbent layer 34 is wood pulp.

For further details on the structure and the method of construction of the second absorbent layer 34, the reader is invited to refer to the U.S. Pat. No. 5,866,226 granted on Feb. 2, 1999 to Tan et al. The contents of this document are hereby incorporated by reference.

Alternatively, the second absorbent layer 34 may include other absorbent materials such as sphagnum peat moss.

Barrier Layer

Underlying the absorbent system 30 is the barrier layer 28 comprising liquid-impervious film material so as to prevent liquid that is entrapped in the absorbent system 30 from egressing the sanitary napkin 10 and staining the wearer's undergarment. The barrier layer 28 is preferably made of polymeric film, such as polyethylene or polyethylene/ethylvinyl acetate (EVA), which are both inexpensive and readily available. The polymeric film is capable of fully blocking the passage of liquid or gas that may emanate from the absorbent system 30. In a variant, breathable films, which allow passage of gases while blocking liquid, may be used. A suitable example is a combination polyethylene/ethylvinyl acetate (EVA) film sold by the Edison Plastics Company in the United States under the commercial designation XP-1167B.

Flaps

The sanitary napkin has flaps 36, 38 extending laterally from the longitudinal sides of the main body and are adapted to be folded over the edges of a crotch portion of a user's undergarment. FIG. 3 illustrates the manner of attaching the flaps 36, 38 to the main body 12 of the sanitary napkin 10. Each flap has a proximal end portion 70 and a distal end portion 72. The proximal end portion 70 is the area of the flap 36, 38 that is adjacent the corresponding longitudinal side 14, 16 of the sanitary napkin 10. The distal end portion 72 is the portion of the flap 36, 38 that is remote from the longitudinal side 14, 16 with which the flap 36, 38 is respectively associated. In addition, each flap 36, 38 also has an outer face 76 and an inner face 74. The inner face 74 is the side of the flap 36, 38 that faces the barrier layer 28 when the flap 36, 38 is in a position such as that shown in FIG. 3, in other words being adjacent or resting against the barrier layer 28. The outer face 76 is the side of the flap 36, 38 that faces away from the barrier layer 28 when the flap 36, 38 rests against the barrier layer 28.

Figure 4:
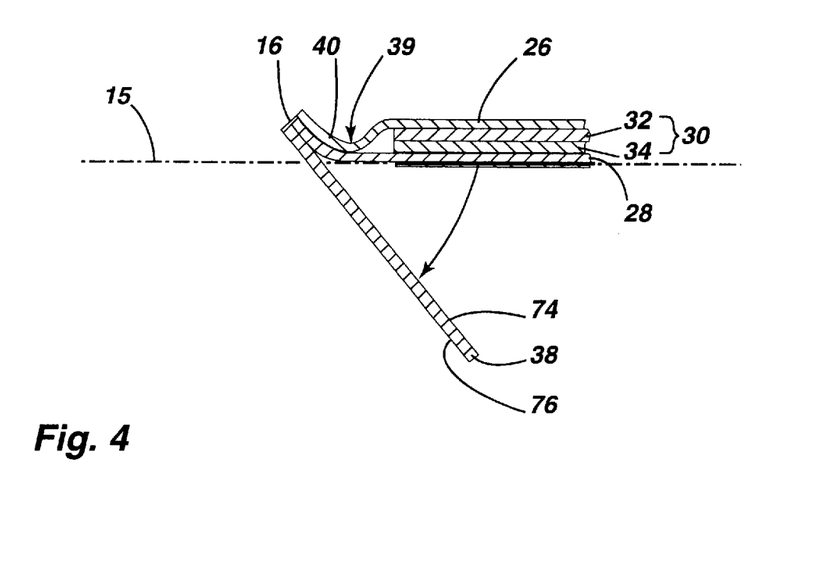
FIG. 4 is a fragmentary cross-sectional view similar to the illustration shown in FIG. 3 with the exception that only a portion of the sanitary napkin is being shown, the sanitary napkin has a stiff flap that is shown as outwardly displaced to cause the flange seal of the sanitary napkin to bend upwardly.

Each flap 36, 38 is affixed to a corresponding longitudinal side 14, 16 of the main body 12 in a cantilever arrangement and at least a portion of the flap possesses sufficient rigidity such as to cause the longitudinal side 14, 16 to fold upwardly when the flap 36, 38 is displaced from a position such as that shown in FIG. 3 to a position as shown in FIG. 4. In the position shown in FIG. 3, the flap 36, 38 acquires a more acute angular relationship with relation to the barrier layer 28 than in the position shown at FIG. 4.

Figure 2:
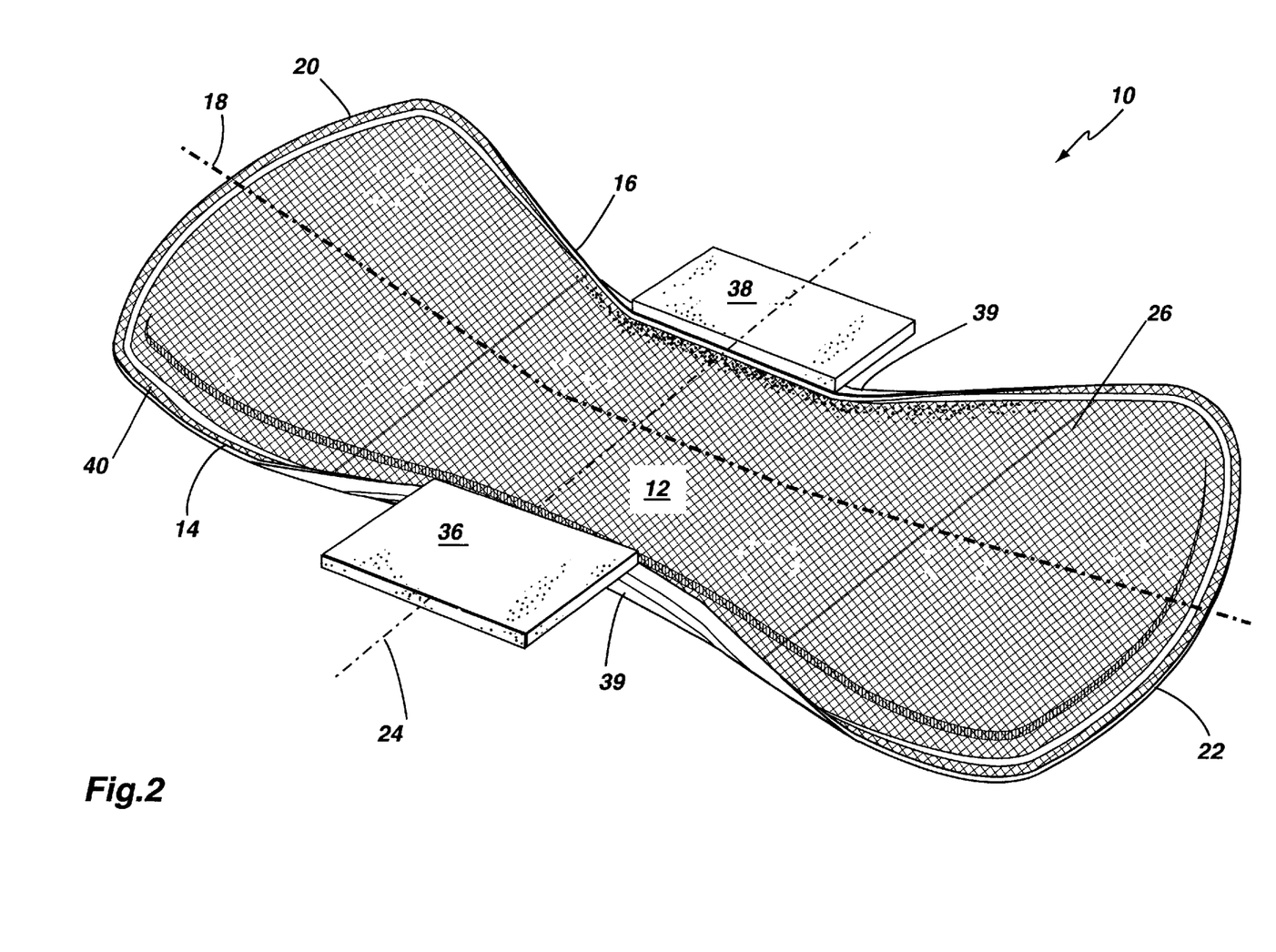
FIG. 2 is a top perspective view of the sanitary napkin shown in FIG. 1, the stiff flaps of the sanitary napkin being shown parted in a position allowing the installment of the sanitary napkin in the crotch portion of the undergarment.

FIG. 2 illustrates the configuration acquired by the main body 12 when both flaps 36, 38 are parted to insert the crotch portion of the undergarment between them. Because of the outward cantilever pivotal displacement of each flap 36, 38, the longitudinal sides 14, 16 fold upwardly as discussed above. The parting of the flaps 36, 38 shown in FIG. 2 is somewhat exaggerated. In practice, it will not be required to part the flaps 36, 38 as much to clear the crotch portion of the undergarment. When the sanitary napkin 10 is installed on the undergarment the flaps 36, 38 are released. Due to the resiliency of the longitudinal sides 14, 16 of the main body 12, the flaps 36, 38 have a tendency to at least partially return to their original position and abut the crotch portion of the undergarment.

The position of the flaps 36, 38 when they rest against the crotch portion of the undergarment generally corresponds to the position of the flap 36, 38 as shown in FIG. 4 for flap 38. In this position of the flaps 36, 38, two beneficial features arise. Firstly, each longitudinal side 14, 16 is raised and forms an upstanding barrier on the main body 12 that impedes the lateral flow of body exudate and can, therefore, reduce the likelihood of failures. Secondly, the flaps 36, 38 are urged against the crotch portion of the undergarment and thus engage the undergarment, which has the effect of stabilizing the sanitary napkin 10 on the undergarment.

Three primary factors determine the extent to which these two beneficial features will manifest themselves, namely: the rigidity of the flaps 36, 38, the rigidity of the longitudinal sides 14, 16, and the manner of physical association between the flaps 36, 38 and the longitudinal sides 14, 16.

Figure 5:
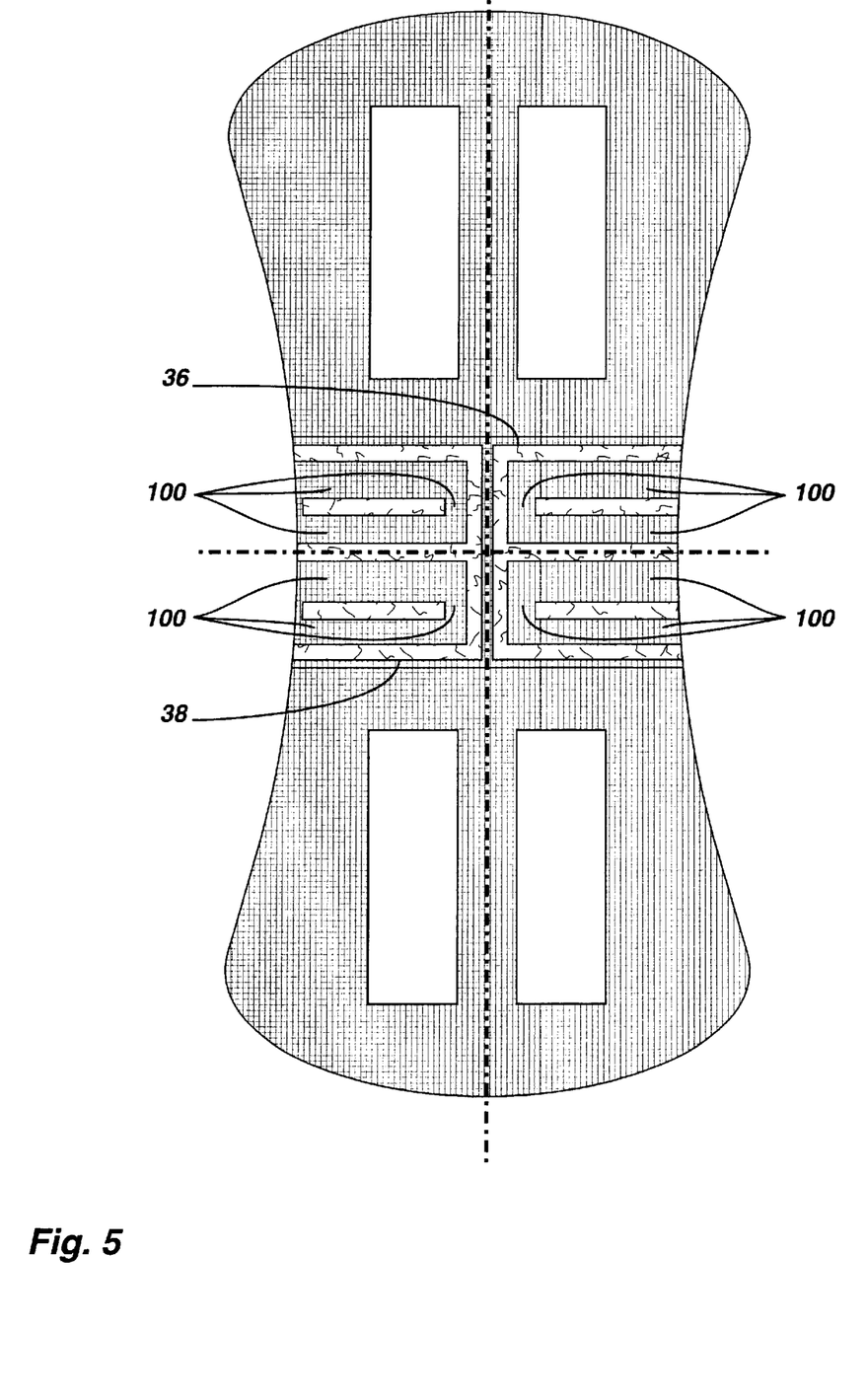
FIG. 5 is a bottom plan view of a sanitary napkin constructed in accordance with a variant.

With regard to the first factor, at least a portion of each flap 36, 38 should possess a rigidity or stiffness sufficient such that when it is displaced outwardly, such displacement causes the longitudinal side 14, 16 physically associated with the flap 36, 38 to fold upwardly. A sufficient rigidity can be obtained by using a material for manufacturing the flap 36, 38 that is inherently rigid or by conditioning the material to enhance its rigidity. In a specific example of implementation, the flaps 36, 38 are made of polymeric foam material. Polymeric foam is commercially available in a wide range of densities and thicknesses from Voltek in Lawrence Mass., USA. Conditioning a material to make it more rigid is generally known in the art and many possibilities exist. One possibility is to laminate a base material with another material to form a layered structure that is more rigid than the base material. Another possibility is to compress the material to densify it, which usually results in a more rigid structure. Yet another possibility is to emboss the base material to create a pattern of localized densification areas that impart additional rigidity. This possibility is illustrated in FIG. 5. The flaps 36, 38 are made of polymeric foam material that has been locally embossed at 100 to donate to the flaps 36, 38 additional rigidity.

A further possibility to increase the rigidity of the flap 36, 38 is to impregnate the material of the flap 36, 38 with a liquid, such as any suitable binder, that makes the base material more rigid when it sets.

With regard to the second factor that is the rigidity of the longitudinal side 14, 16, if the longitudinal side is very soft and yields readily to bending pressure, a flap 36, 38 of a lesser rigidity will be needed to cause formation of an upstanding barrier. At the same time the flap 36, 38 will be urged against the undergarment with less intensity than if the longitudinal side 14, 16 manifests a strong resiliency. The rigidity of the longitudinal sides 14, 16 depends upon several factors, namely: the number of layers forming the lateral side 14, 16, the rigidity of the individual layers, the way those individual layers are bonded to one another, among others.

With regard to the third factor that is the manner of physical association between the flaps 36, 38 and the longitudinal sides 14, 16, the following observations can be made. Different possibilities exist to physically associate the flap 36, 38 to the corresponding longitudinal side 14, 16 such that when the flap 36, 38 is displaced outwardly, its longitudinal side 14, 16 is folded upwardly. One such possibility is to directly bond the flap 36, 38 to the longitudinal side 14, 16. Another possibility is to fasten the flap 36, 38 to the longitudinal side through an intermediate component. Under the first possibility, the inner face 74 of the proximal end portion of the flap 36, 38 is bonded to the flange seal 40. The joint may be made by means of adhesives, heat-bonding, ultrasonic bonding, radio frequency sealing, mechanical crimping, and the like and combinations thereof.

The surface area of the bond between the flap 36, 38 and the longitudinal side 14, 16 along flange seal 40 influences to what extend the longitudinal side 14, 16 will fold upwardly when the flap 36, 38 is displaced outwardly. In particular, the width of the bond surface area (the width is measured along an imaginary line that is transverse to the longitudinal side 14, 16) should be sufficient to cause the formation of an upstanding barrier. Under a specific and non-limitative example of implementation, the width of the bond surface area generally corresponds to the width of the flange seal 40.

Figure 7:
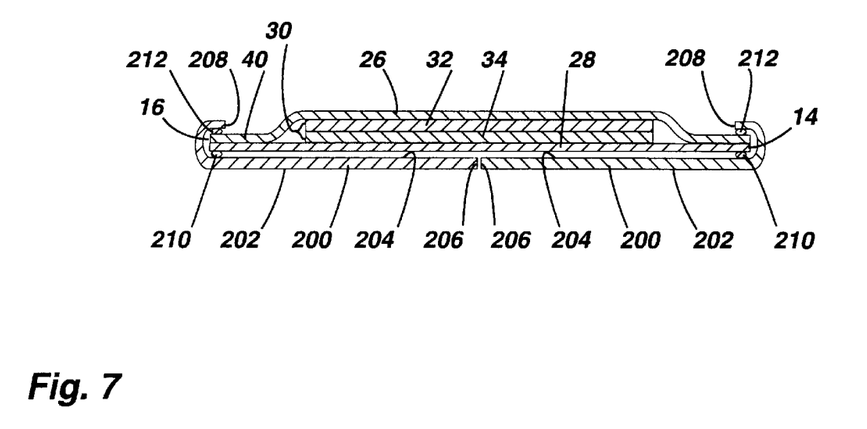
FIG. 7 is a cross-sectional view of a sanitary napkin in accordance with a variant.

A possible variant under the first possibility is illustrated in FIG. 7 that shows the sanitary napkin 10 in cross section. It that figure, all the components of the sanitary napkin 10 that are identical of similar to the components previously illustrated and described will be designated by the same reference numerals. Under this variant, the flaps 200 are also associated with the longitudinal sides 14, 16 in a cantilever arrangement but the proximal end portion 208 of each flap 200 is folded over the cover layer 26 such that the proximal end portion 208 forms a loop receiving the respective longitudinal side 14, 16. More specifically, the inner face 204 of each flap 200 is first bonded at the barrier layer 28 at location 210, then folded upwardly so as to overlay the cover layer 26 and bond with the cover layer 26 at location 212. This realization offers the benefit of a stronger attachment between the flaps 200 and the longitudinal sides 14, 16.

The reader skilled in the art will recognize that by varying the three factors discussed earlier, the behavior of the sanitary napkin 10 can be altered to suit specific applications.

Referring back to FIG. 1, the flaps 36, 38 are bonded to the main body 12 with their respective distal end portions 72 retained to one another by a frangible bond. This allows the sanitary napkin 10 to be placed on the undergarment without using the flaps, if the user so desires. Alternatively, by separating the distal end portions 72 from one another, the flaps 36, 38 become operational. In practice, the flaps 36, 38 can be manufactured as a single unit having across its center a line of weakness 102 that allows the wearer to separate the unit in two identical halves. The line of weakness 102 can be a line of perforations or any other physical treatment of the material that creates a local fragile area that will rupture when pulled apart.

In order to enhance the comfort potential of the sanitary napkin 10 the flaps 36, 38 may be provided with specific materials or treatments designed to reduce the possibility of irritation of the skin at the area where the flaps 36, 38 contact the thighs of the wearer. One possibility is to laminate the outer face 76 of the flaps 36, 38 with a material that is soft and non-irritating. One such example is a non-woven fabric. Another possibility is to treat the outer face 76 such that it presents a non-irritating surface. Such a treatment may be designed to create a very smooth surface or a surface that is soft and compliant. At the same time, a different treatment may be provided on the inner face 74 to make that surface rougher such as to reduce slippage between the flap 36, 38 and the undergarment. It is within the reach of a person skilled in the art to select the treatment method to create the desired surface finishes described above.

Another possible refinement that can be considered is to apply on the inner face 74 a release coating such as silicone coating to prevent accidental bonding between the flap 36, 38 and the positioning adhesive of the main body 12. The positioning adhesive is discussed below.

Adhesives

Referring back to FIG. 1, the barrier layer 28 is provided with an area of adhesive material 25 to retain the sanitary napkin 10 on the undergarment of the wearer. The area of adhesive material 25 is rectangular and extends over the major part of the length of the main body 12. Release paper 104 covers the adhesive material 25. A suitable adhesive is the composition designated HL-1491 XZP commercially available from H. B. Fuller Canada, Toronto, Ontario, Canada. The release paper is of conventional construction (silicone coated wet-laid Kraft wood pulp) and suitable papers are available from Tekkote Corporation (Leonia, N.J., USA), and bear the designation FRASER 30#/61629.

Figure 6:
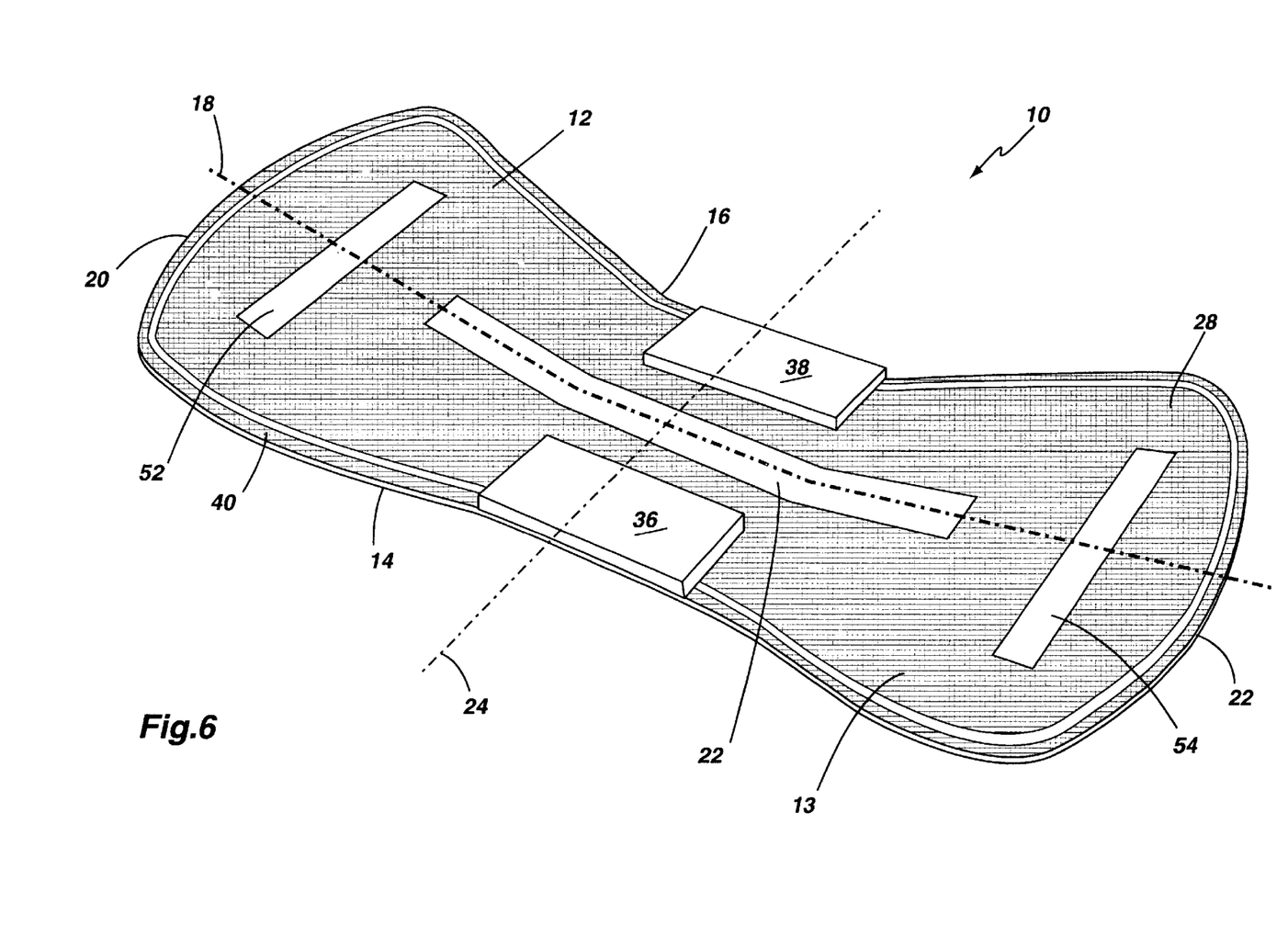
FIG. 6 is a bottom perspective view of a sanitary napkin constructed in accordance with a further variant.

In the example of implementation of the invention illustrated in FIG. 1, the adhesive material 25 and the release paper 104 pass under the flaps 36, 38. In a possible variant shown in FIG. 6, the flaps 36, 38 are shorter such that a space is defined between their distal end portions 72. A zone of adhesive material 22 extends in that space. The advantage of this form of implementation is that there is little risk of accidentally adhering the flaps 36, 38 to the zone of adhesive material 22. In addition to this zone of adhesive material 22, the sanitary napkin 10 is provided with two additional zones of adhesive material 52 and 54 near the transverse end portions 20 and 22 of the main body 12. The zones of adhesive material 22, 52 and 54 are covered by release papers, not shown in the drawings.

Test Procedures

Figure 8:
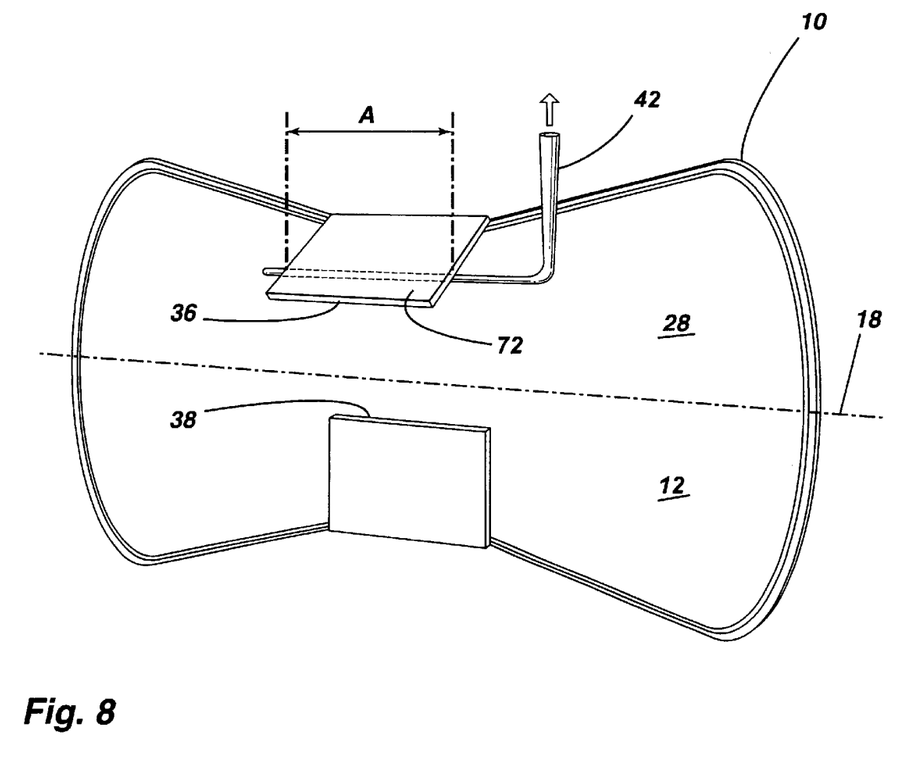
FIG. 8 is a perspective view of a testing apparatus for measuring the cantilever authority of a tab.

FIG. 8 illustrates a test set-up to measure the cantilever authority of the flap 36, 38. The test set-up includes a suitable support (not shown) to hold the sanitary napkin 10 in a vertical position. An angled probe 42 is slipped under the flap 36 and the dimension A noted. A is the length of the flap 36 (measured along the centerline 18) at the area where it contacts the horizontal segment of the probe 42. To properly assess the dimension A, the horizontal segment of the probe 42 should be placed as close as possible to the barrier layer 28 without rubbing too much against the barrier layer. The objective is to avoid that friction between the horizontal segment of the probe 42 and the barrier layer 28 influences significantly the test results. In addition, the horizontal segment of the probe 42 is placed vertically as close as possible to the location where the flap 36 is attached to the main body 12.

The probe 42 is then displaced vertically at a constant speed and the force at different vertical positions of the probe 42 recorded. The movement is stopped when the horizontal segment of the probe 42 has cleared the distal end portion 72. The peak force value is extracted and divided by the dimension A to obtain a result expressed in grams per centimeter. The test is performed a total of ten times and the results averaged to obtain the cantilever authority for the flap 36.

Although various embodiments have been illustrated, this was for the purpose of describing, but not limiting, the invention. Various modifications will become apparent to those skilled in the art and are within the scope of this invention, which is defined more particularly by the attached claims.

I claim:

1. A sanitary napkin for placement in a crotch portion of an undergarment, said sanitary napkin comprising:
    i) a main body having a pair of opposite longitudinal sides and a pair of opposite transverse sides, said main body including:
        1) a fluid permeable body facing layer;
        2) an absorbent layer underneath said fluid permeable body facing layer;
        3) a liquid impermeable undergarment facing layer underneath said absorbent layer,
    ii) a first flap affixed to a first longitudinal side of said main body in a cantilever arrangement;
    iii) a second flap affixed to a second longitudinal side of said main body in a cantilever arrangement, wherein said first flap and said second flap each have a first position and a second position, said first position said flap acquiring a more acute angular relationship to said liquid impermeable undergarment facing layer than in said second position; said flap having a rigidity sufficient to cause the longitudinal side to fold upwardly when said flap is in said second position, wherein when each flap is in said second position and the crotch portion of the undergarment is placed between said flaps, each longitudinal side of said main body is operative to urge the respective flap toward the crotch portion of the under garment.

2. A sanitary napkin as defined in claim 1, wherein each flap has a proximal end portion attached to a respective longitudinal side of said main body and a distal end portion remote from said proximal end, each flap further including an inner face oriented toward said main body and an outer face oriented away from said main body, a portion of said inner face adjacent said proximal end portion being attached to the respective longitudinal side of said main body.

3. A sanitary napkin as defined in claim 2, wherein said inner face is attached to said liquid impermeable undergarment facing layer.

4. A sanitary napkin as defined in claim 3, wherein said inner face is attached to said liquid impermeable undergarment facing layer by a method selected in the group consisting of adhesive bonding, heat-bonding, ultrasonic bonding, radio frequency bonding, mechanical crimping and combinations thereof.

5. A sanitary napkin as defined in claim 2, wherein the distal end portions of said flaps are retained to one another by a frangible bond.

6. A sanitary napkin as defined in claim 1, wherein each flap includes polymeric foam material.

7. A sanitary napkin as defined in claim 1, wherein each flap includes at least one embossed area enhancing a rigidity of the tab.

8. A sanitary napkin as defined in claim 1, wherein said absorbent layer includes a plurality of superposed layers.

9. A sanitary napkin as defined in claim 1, wherein said fluid permeable body facing layer and said liquid impermeable undergarment facing layer are united to one another to form a flange seal, each longitudinal side of said main body including a portion of said flange seal.

10. A sanitary napkin for placement in a crotch portion of an undergarment, said sanitary napkin comprising:

i) a main body having a pair of opposite longitudinal sides and a pair of opposite transverse sides, said main body including:
      1) a fluid permeable body facing layer;
      2) an absorbent layer underneath said fluid permeable body facing layer;
      3) a liquid impermeable undergarment facing layer underneath said absorbent layer,
   ii) a first flap affixed to a first longitudinal side of said main body in a cantilever arrangement;
   iii) a second flap affixed to a second longitudinal side of said main body in a cantilever arrangement, wherein said first flap and said second flap each have a first position and a second position, said first position said flap acquiring a more acute angular relationship to said liquid impermeable undergarment facing layer than in said second position; said flap having a rigidity sufficient to cause the longitudinal side to fold upwardly when said flap is in said second position, wherein each flap further comprises a proximal end portion attached to a respective longitudinal side of said main body and a distal end portion remote from said proximal end, an inner face oriented toward said main body and an outer face oriented away from said main body, a portion of said inner face adjacent said proximal end portion being attached to the respective longitudinal side of said main body, wherein proximal end portion forms a loop that receives the respective longitudinal side of said main body.

11. A sanitary napkin as defined in claim 10, wherein said loop is retained to the respective longitudinal side of said main body at two spaced apart locations.

12. A sanitary napkin as defined in claim 11, wherein said loop is retained at said body facing layer and at said liquid impermeable undergarment facing layer.

\* \* \* \* \*